(12) United States Patent
van den Engh et al.

(10) Patent No.: US 8,753,573 B2
(45) Date of Patent: Jun. 17, 2014

(54) MULTI-WAY SORTER SYSTEM AND METHOD

(75) Inventors: Gerrit Jan van den Engh, Seattle, WA (US); Timothy Wayne Petersen, Seattle, WA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/457,181

(22) Filed: Apr. 26, 2012

(65) Prior Publication Data

US 2012/0276621 A1 Nov. 1, 2012

Related U.S. Application Data

(60) Provisional application No. 61/480,867, filed on Apr. 29, 2011.

(51) Int. Cl.
| | |
|---|---|
| *G01N 33/00* | (2006.01) |
| *B01L 3/02* | (2006.01) |
| *C12M 3/00* | (2006.01) |
| *C12M 1/42* | (2006.01) |
| *G01N 33/48* | (2006.01) |
| *G01N 1/12* | (2006.01) |

(52) U.S. Cl.
USPC ............ 422/73; 422/521; 436/63; 73/864.59; 435/285.2

(58) Field of Classification Search
USPC ........ 422/538, 539, 509, 521; 436/63; 73/864
See application file for complete search history.

(56) References Cited

U.S. PATENT DOCUMENTS

| | | | |
|---|---|---|---|
| 5,150,313 A | 9/1992 | van den Engh et al. | |
| 5,407,794 A * | 4/1995 | Kass | 436/63 |
| 5,466,572 A | 11/1995 | Sasaki et al. | |
| 5,475,487 A | 12/1995 | Mariella, Jr. et al. | |
| 5,489,506 A * | 2/1996 | Crane | 435/2 |
| 6,003,678 A | 12/1999 | Van den Engh | |
| 6,211,477 B1 * | 4/2001 | Cardott et al. | 209/127.4 |
| 7,679,039 B2 | 3/2010 | van den Engh et al. | |
| 7,728,974 B2 | 6/2010 | van den Engh et al. | |
| 2002/0119558 A1 | 8/2002 | Seidel et al. | |
| 2002/0167656 A1 | 11/2002 | van den Engh | |
| 2002/0186375 A1 | 12/2002 | Asbury et al. | |
| 2006/0002824 A1 * | 1/2006 | Chang et al. | 422/100 |
| 2007/0117086 A1 * | 5/2007 | Evans et al. | 435/4 |
| 2009/0176271 A1 * | 7/2009 | Durack et al. | 435/40.5 |
| 2010/0297759 A1 | 11/2010 | Kanda | |

FOREIGN PATENT DOCUMENTS

| | | | |
|---|---|---|---|
| EP | 0154687 | A2 | 9/1985 |
| WO | WO 2010-095391 | A1 | 8/2010 |

* cited by examiner

*Primary Examiner* — Jill Warden
*Assistant Examiner* — Brittany Fisher
(74) *Attorney, Agent, or Firm* — Bozicevic, Field & Francis LLP; Bret E. Field; Colin Thom (57) ABSTRACT

Provided herein are improved multi-way cell sorter systems and methods. For example, provided are systems and methods for the collection of cells that are sorted in multiple directions. The systems and methods allow for the construction of a multi-way sorter (e.g., a ten-way sorter in the space that currently only allows four-way sorting). In addition the device may actively sense the arrival of drops (with cells of interest) at a sample tube, and trigger an alarm when the drops' arrivals deviate from an expected pattern.

21 Claims, 6 Drawing Sheets

MULTI-WAY SORTER SYSTEM AND METHOD

CROSS-REFERENCE TO RELATED APPLICATIONS

Pursuant to 35 U.S.C. §119(e) this application claims priority to the filing date of U.S. Provisional Patent Application Ser. No. 61/480,867 filed Apr. 29, 2011; the disclosure of which application is herein incorporated by reference.

INTRODUCTION

The present invention relates to flow cytometers and instruments for high speed identification and sorting of particles, such as cells.

Flow cytometry is a valuable method for the analysis and isolation of biological particles such as cells and constituent molecules. As such it has a wide range of diagnostic and therapeutic applications. The method utilizes a fluid stream to linearly segregate particles such that they can pass, single file, through a detection apparatus. Individual cells can be distinguished according to their location in the fluid stream and the presence of detectable markers. Thus, a flow cytometer can be used to produce a diagnostic profile of a population of biological particles.

Isolation of biological particles has been achieved by adding a sorting or collection capability to flow cytometers. Particles in a segregated stream, detected as having one or more desired characteristics, are individually isolated from the sample stream by mechanical or electrical removal. A common flow sorting technique utilizes drop sorting in which a fluid stream containing linearly segregated particles is broken into drops and the drops containing particles of interest are electrically charged and deflected into a collection tube by passage through an electric field.

Typically, the linearly segregated particles in the stream are characterized as they pass through an observation point situated just below the nozzle tip. Once a particle is identified as meeting one or more desired criteria, the time at which it will reach the drop break-off point and break from the stream in a drop can be predicted. Ideally, a brief charge is applied to the fluid stream just before the drop containing the selected particle breaks from the stream and then grounded immediately after the drop breaks off. The drop to be sorted maintains an electrical charge as it breaks off from the fluid stream, and all other drops are left uncharged. The charged drop is deflected sideways from the downward trajectory of the other drops by an electrical field and collected in a sample tube. The uncharged drops fall directly into a drain.

Droplet sorters deflect drops that contain cells of interest by applying a charge (typically 50-150 volts) to the drops. The drops are deflected by an electrostatic field and, depending on the charge, follow different trajectories so that that arrive at a collection tube. The cells can be distributed over multiple groups by applying different charges, each discrete charge guiding a drop to a particular tube. Originally cell populations were divided in to two groups: a left and a right sort. lately the number of sort directions (groups) has been increased to 4 (most sorters) or even 6. An example flow cytometer system having multiple collection tubes is provided in U.S. Pat. No. 5,483,469, which is incorporated herein by reference in its entirety.

The number of sort directions is currently limited by the number of collection tubes that can be placed on the axis along which the drops are distributed. The typical drop spread in one direction is about 22 mm The tube centers are 14 mm apart so that with difficulty three groups can be sorted.

The tube size is not the only factor in limiting the number of sort directions. It is also difficult to place sorted drops in close proximity because the drops carry a charge. As such, charged drops will repel each other. As the drops accumulate into a bigger volume the charge grows disproportionally faster. Due to the accumulation of charge, the sorted cell volume tends to want to break into smaller drops. These drops repel and push away each other causing drops to jump around erratically, sometimes even jumping into adjacent tubes with drops of opposite charge, thus severely affecting the purity of a sort.

SUMMARY

Provided herein are improved multi-way cell sorter systems and methods. For example, provided are systems and methods for the collection of cells that are sorted in multiple directions. The systems and methods allow for the construction of a multi-way sorter (e.g., a ten-way sorter in the space that currently only allows four-way sorting). In addition the device may actively sense the arrival of drops (with cells of interest) at a sample tube, and trigger an alarm when the drops' arrivals deviate from an expected pattern. Such a signal could be used to move the collection tubes into a safe position preventing contamination of the sorted samples. This device is desirable for clinical sorting. The device is also suitable as a disposable unit.

The systems and methods presented provide a cure for the drop accumulation problem, and allow deflected drop streams to be placed in closer proximity without affecting stream stability.

Exemplary systems and methods presented include a sorted drop receptacle (or carrier) that consists of a row of sort tubes (or deflection tubes) that are open at both sides. The deflected drops are accordingly aimed at the inside of a sort tube. Each sort tube is individually grounded so that the deflection charge on the drops is harmlessly deflected to ground. Thus the drops no longer carry a charge and can grow into larger drops that slide down the sort tube. Each sort tube is inserted in an opening of a sample collection tube. Since the sort tubes can be bent, the collection tubes no longer need to be placed along a line, but can be configured in a staggered pattern. As such, a collection area that once held three tubes in a straight line, can now accommodate five tubes in a staggered configuration. Since the sort tubes can be narrower than the collection tubes, the tops of the five sort tubes can be placed along a 20 mm line, with the bottom of the tubes leading to five staggered collection tubes place in a 20×30 mm area.

In one embodiment, an arrangement of ten collection tubes with ten sort tubes can be fitted on the area of a standard microscope slide. A plastic carrier with the dimensions of a microscope slide may hold about ten thin walled stainless steel deflection tubes. The ten deflection tubes lead to ten plastic collection tubes that are attached to the bottom of the plastic carrier. The whole unit may be made available as one sterile and disposable unit.

The top of the sort tubes may also be closed off when appropriate. For example, the system can monitor the arrival of drops in the sort fractions by measuring the charge that is deposited in the individual metal sort tubes. If the metal sort tubes are connected to ground via a current-to-voltage converter, with a variable integration time, the voltage measured at each sort tube reflects the number of drops that are deposited in each tube per-unit-time. A computer program can be configured to predict the expected voltage generated for each sort direction. If the measured voltage differs from the expected voltage, the computer can instruct a stepper motor to cover the sort tubes, or move the collection tray into a safe, covered (or otherwise deactivated) position, preventing contamination of the sorted fractions with unwanted cells.

The carrier presented may be used as a multi-way (e.g. ten-way) sorter in all current influx sorters, without the need for any changes to the influx design. The possibility to continuously monitor the number of cells that are deposited in each tube also provides a safeguard that currently is not available on cell sorters. This control device should be very desirable for sorts that require a high degree of confidence in the purity of the cell fractions.

BRIEF DESCRIPTION OF THE FIGURES

The accompanying drawings, which are incorporated herein, form part of the specification. Together with this written description, the drawings further serve to explain the principles of, and to enable a person skilled in the relevant art(s), to make and use systems and methods in accordance with the present invention.

DETAILED DESCRIPTION

The following detailed description of the figures refers to the accompanying drawings that illustrate an exemplary embodiment of a carrier for a cell sorter system. Other embodiments are possible. Modifications may be made to the embodiments described herein without departing from the spirit and scope of the present invention. Therefore, the following detailed description is not meant to be limiting.

Figure 1:
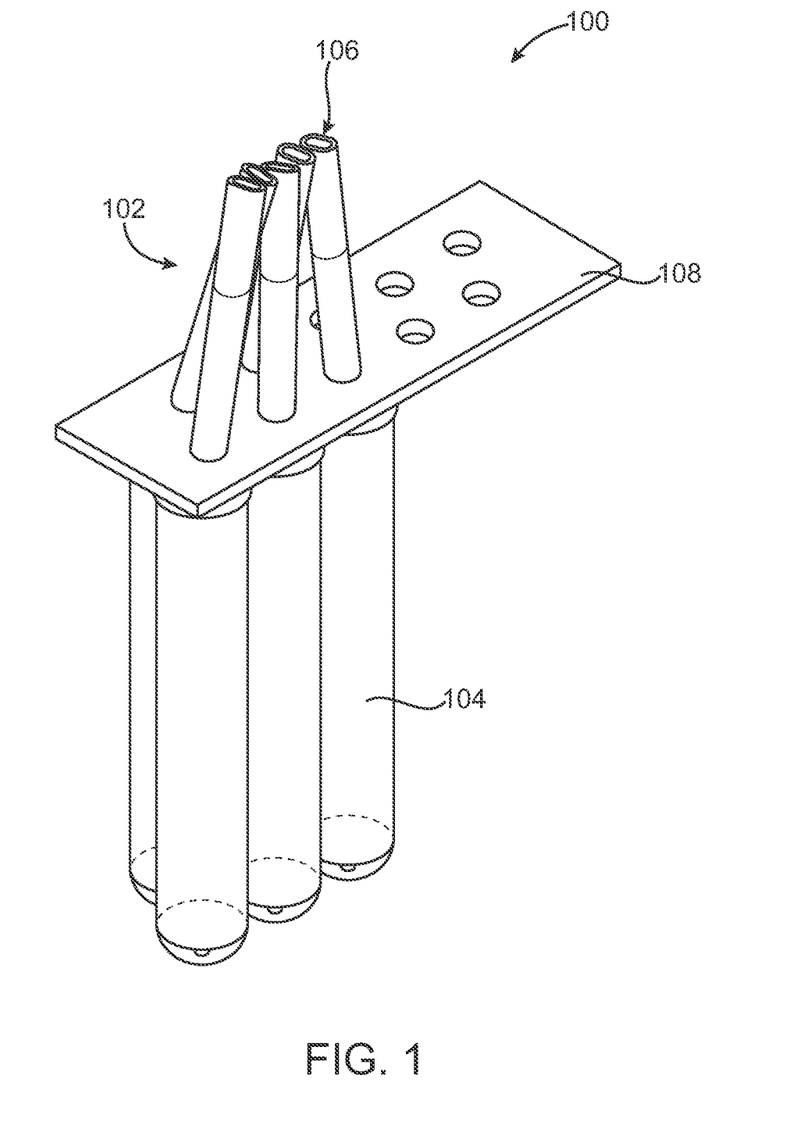
FIG. 1 is a perspective view of a portion of a multi-way cell sorter carrier, in accordance with one embodiment presented herein.
Figure 2:
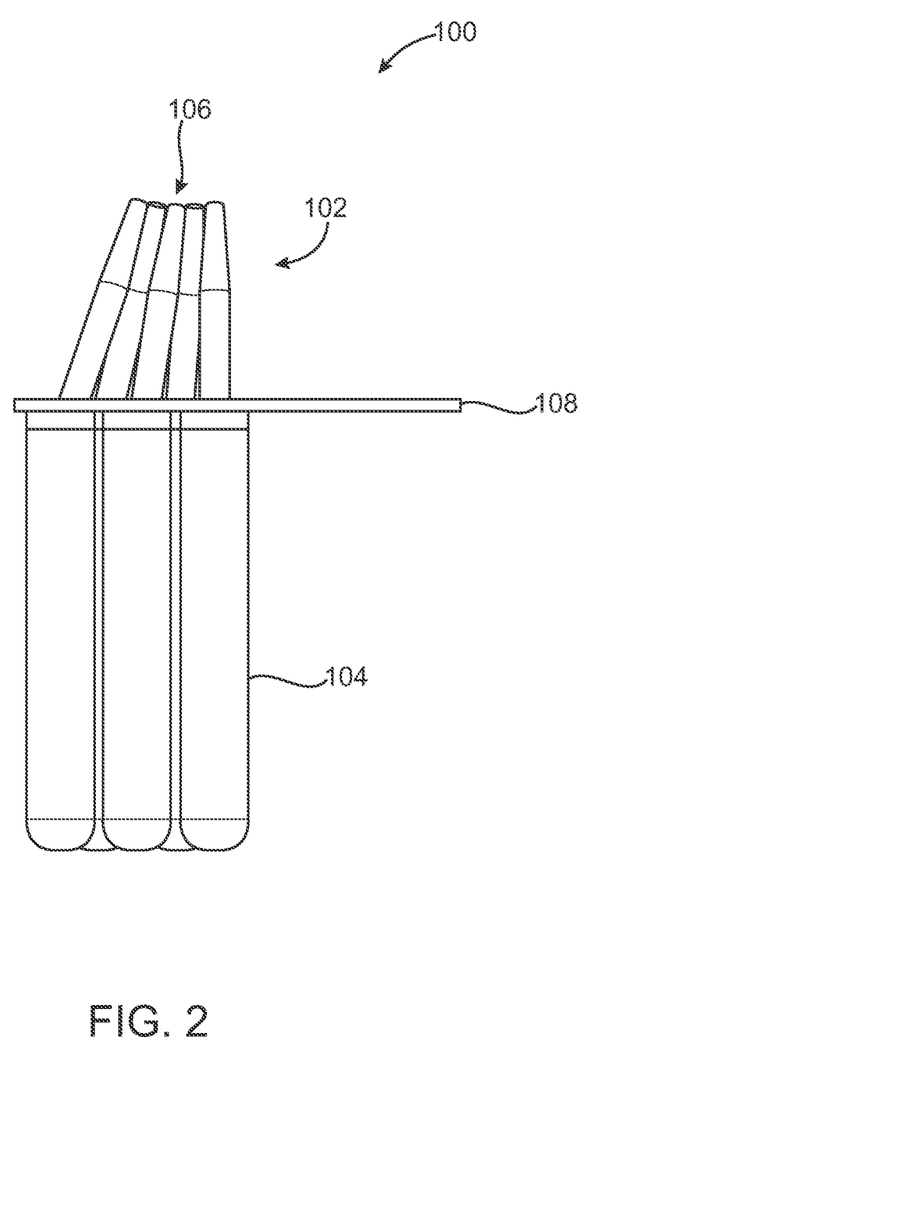
FIG. 2 is a side view of a portion of the multi-way cell sorter carrier of FIG. 1.
Figure 3:
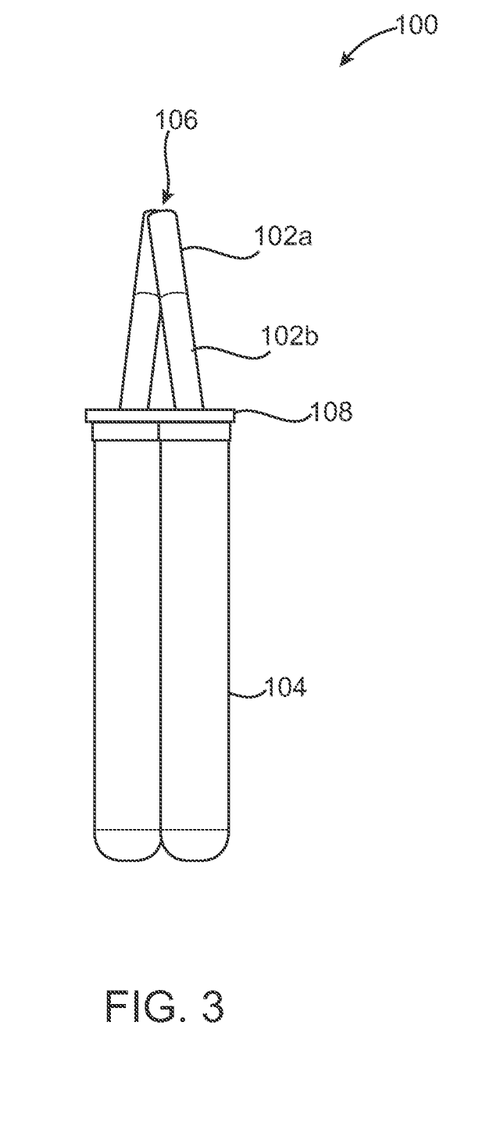
FIG. 3 is a front view of a portion of the multi-way cell sorter carrier of FIG. 1.
Figure 4:
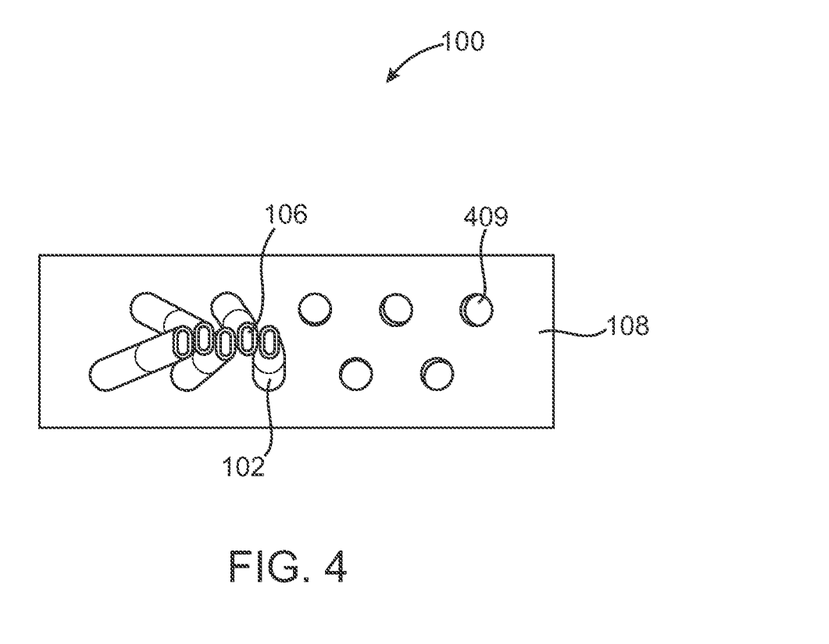
FIG. 4 is a top view of a portion of the multi-way cell sorter carrier of FIG. 1.

FIG. 1 is a perspective view of a portion of a multi-way cell sorter carrier 100, in accordance with one embodiment presented herein. FIG. 2 is a side view of a portion of multi-way cell sorter carrier 100. FIG. 3 is a front view of a portion of multi-way cell sorter carrier 100. FIG. 4 is a top view of a portion of multi-way cell sorter carrier 100. Carrier 100 may be incorporated into a cell sorter system. An exemplary cell sorter system is provided in U.S. Pat. No. 5,483,469, which is incorporated herein by reference in its entirety.

In the embodiment shown, carrier 100 includes a plurality of deflection (or sort) tubes 102 and corresponding collection tubes 104. Each deflection tube 102 is hollow, with openings at both ends. Openings 106 of the deflection tubes 102 are aligned collinearly with one another, along an axis of the deflection. As such, when carrier 100 is incorporated into a cell sorter system, openings 106 of deflection tubes 102 receive deflected charged droplets.

A second opening of each deflection tube 102 is positioned with respect to a corresponding opening in a collection tube 104. As such, charged droplets received within deflection tubes 102 slide into collection tubes 104. Collection tubes 104 are preferably positioned in a staggered arrangement in order to maximize the spacing and number of collection tubes used in carrier 100. To facilitate positioning of deflection tubes 102 and collection tubes 104, and/or to secure the connection between deflection tubes 102 and collection tubes 104, a carrier plate 108 is used. As shown, only five deflection tubes 102 and five collection tubes 104 are presented. However, in one embodiment, up to ten or more deflection tubes and collection tubes may be used.

In one embodiment, each deflection tube 102 is formed of an electrically conductive material (e.g., a metal, such as, stainless steel). Each collection tube 104 may be formed of a lightweight plastic material. Carrier plate 108 may be formed of a plastic material.

Figure 5:
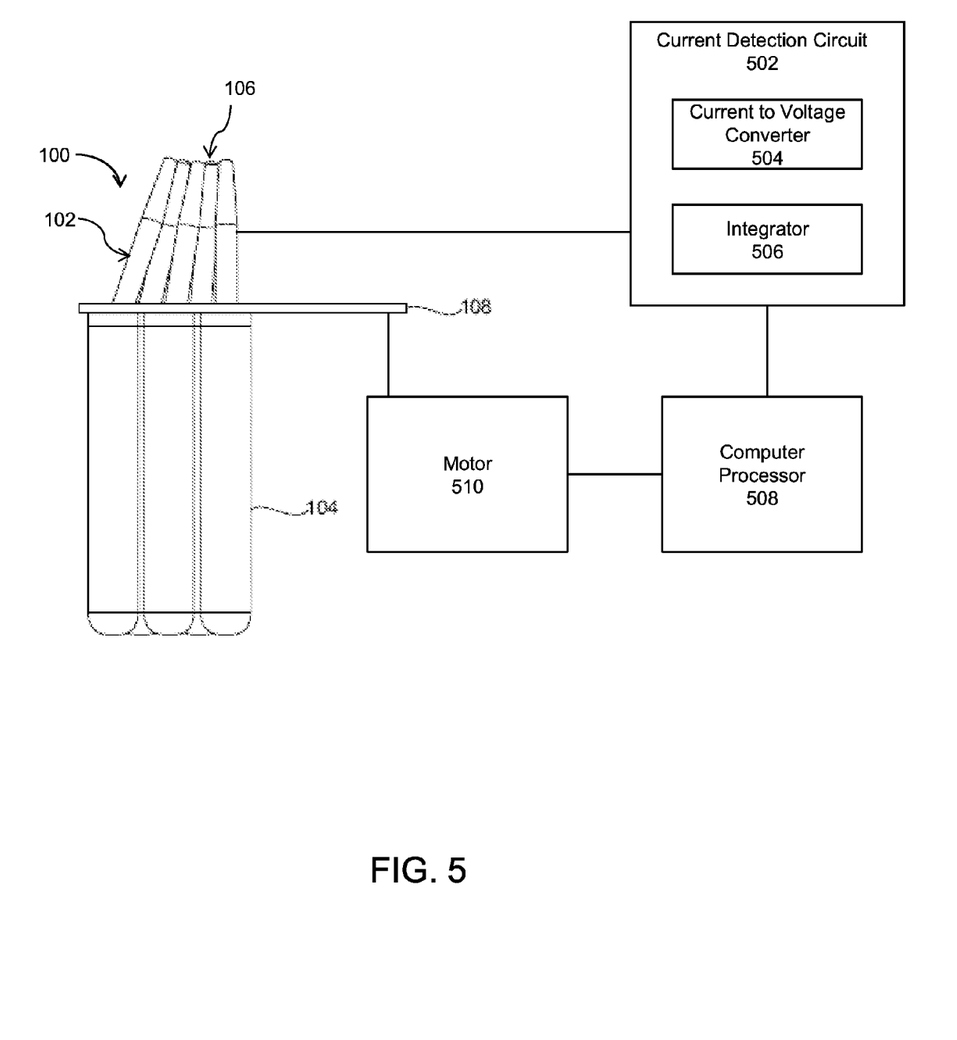
FIG. 5 is a schematic view of the multi-way cell sorter carrier of FIG. 1 coupled to a current detection circuit.
Figure 6:
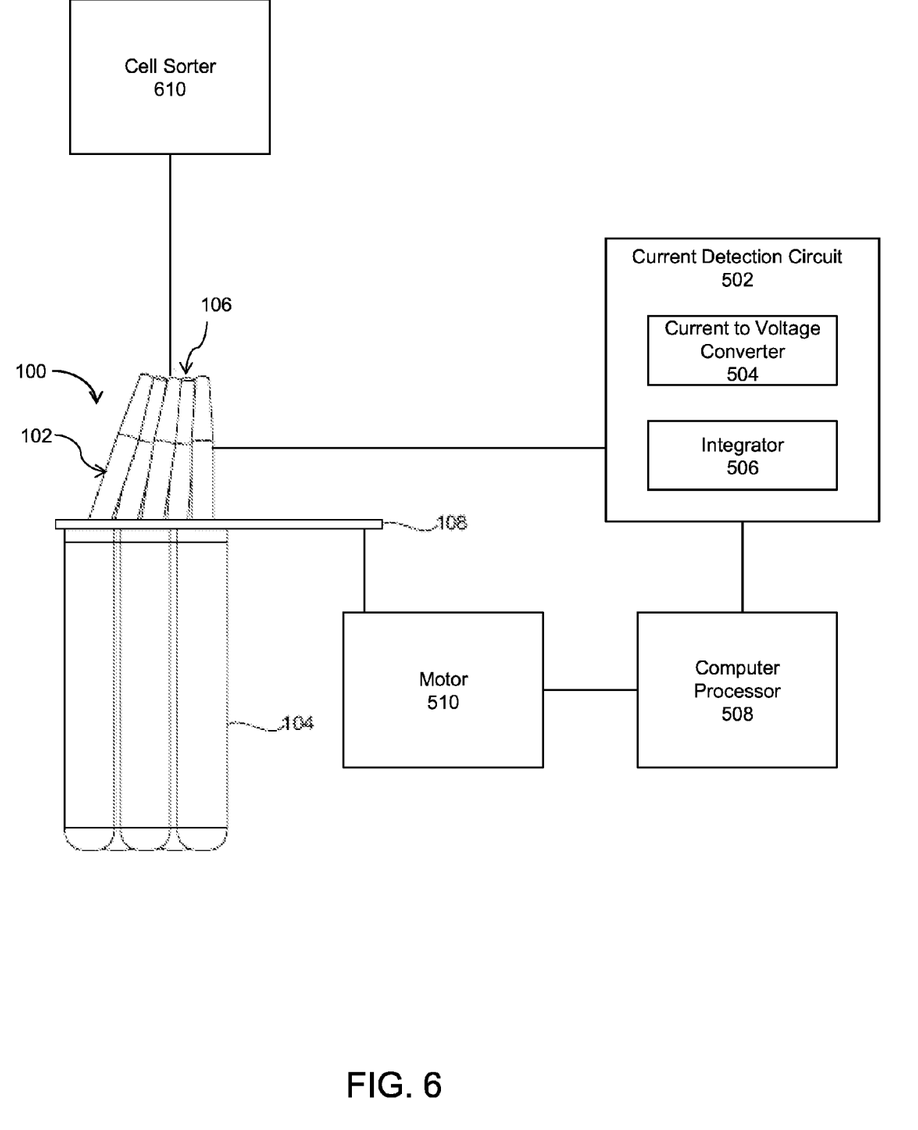
FIG. 6 is a schematic view of the multi-way cell sorter carrier of FIG. 5 incorporated into a cell sorter system.

In another embodiment, each the deflection tube 102 is further coupled to a current-to-voltage converter (CVC) (not shown), which is appropriately grounded. The grounding of the CVC allows for the removal of the charge of the drops received in the deflection tube 102. Further, CVC allows for the measurement of current at deflection tube 102, which is a function of the charged droplet arriving at deflection tube 102. As such, the arrival of drops at carrier 100 can be monitored by measuring the charge that is deposited in the individual deflection tubes 102. If the deflection tubes 102 are connected to ground via CVC, with a variable integration time, the voltage measured at each deflection tube reflects the number of drops that are deposited in each tube per-unit-time. A computer program can be configured to predict the expected voltage generated for each sort direction. If the measured voltage differs from the expected voltage, the computer can instruct a stepper motor to cover the carrier, or move the carrier into a safe, covered, and/or deactivated position, preventing contamination of the carrier with unwanted cells.

In yet another embodiment, each deflection tube 102 may include two segmented pieces 102a, 102b. The segmentation of the deflection tube may be formed by a "bend" in the tube. Since the deflection tubes can be bent, the collection tubes no longer need to be placed along a line, but can be configured in a staggered pattern. As such, a collection area that once held three tubes in a straight line, can now accommodate five tubes in a staggered configuration. Since the deflection tubes can be narrower than the collection tubes, the tops of the five deflection tubes can be placed along a 20 mm line, with the bottom of the tubes leading to five staggered collection tubes placed in a 20×30 mm area.

In still another embodiment, there is provided a carrier for receiving cells sorted from a cell sorter system. The carrier includes a plurality of hollow deflection tubes and a plurality of corresponding collection tubes. Each deflection tube includes a first opening at a first end and a second opening at a second end. The first opening of each deflection tube is aligned with the first opening of an adjacent deflection tube such that the first openings are all collinear. The second openings of the plurality of deflection tubes are staggered with respect to one another. Each collection tube includes an opening positioned to receive a cell passed through and exiting a corresponding deflection tube. In one embodiment, each deflection tube and/or each collection tube is electrically insulated. In one embodiment, the carrier further includes a current detection circuit coupled to at least one deflection tube, or a current detection circuit coupled to each deflection tube. The current detection circuit may further include a current-to-voltage converter to detect the presence of a charged drop entering the deflection tube, and/or an integrator to detect a number of drops per-unit-time entering the deflection tube. Each deflection tube may be formed of a metallic material. Each collection tube may be formed of a plastic material.

In one embodiment, the carrier includes ten or more deflection tubes and ten or more corresponding collection tubes.

Further, there is provided a method for configuring a carrier for receiving cells sorted by a cell sorter system. The method includes aligning a plurality of hollow deflection tubes such that a first open end of each deflection tube is positioned collinearly with a first open end of an adjacent deflection tube. A second open end of each deflection tube is positioned staggered with respect to a second open end of an adjacent deflection tube. The method further includes positioning a plurality of corresponding collection tubes such that an opening for each collection tube is positioned to receive a cell passed through and exiting a corresponding deflection tube. Each deflection tube may be electrically insulated. Each collection tube may be electrically insulated. The method may further include coupling a current detection circuit to at least one deflection tube, or coupling a current detection circuit to each deflection tube. The current detection circuit may include: a current-to-voltage converter to detect the presence of a charged drop entering the deflection tube; and/or an integrator to detect a number of drops per-unit-time entering the deflection tube. Each deflection tube may be formed of a metallic material. Each collection tube may be formed of a plastic material. The carrier may be configured to include ten or more deflection tubes and ten or more corresponding collection tubes.

Conclusion

The foregoing description of the invention has been presented for purposes of illustration and description. It is not intended to be exhaustive or to limit the invention to the precise form disclosed. Other modifications and variations may be possible in light of the above teachings. The embodiments were chosen and described in order to best explain the principles of the invention and its practical application, and to thereby enable others skilled in the art to best utilize the invention in various embodiments and various modifications as are suited to the particular use contemplated. It is intended that the appended claims be construed to include other alternative embodiments of the invention; including equivalent structures, components, methods, and means.

It is to be appreciated that the Detailed Description section, and not the Summary and Abstract sections, is intended to be used to interpret the claims. The Summary and Abstract sections may set forth one or more, but not all exemplary embodiments of the present invention as contemplated by the inventor(s), and thus, are not intended to limit the present invention and the appended claims in any way.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present invention and are disclosed herein just as if each and every such sub-combination of chemical groups was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

What is claimed is:

1. A carrier for receiving cells sorted from a cell sorter system, the carrier comprising:

a plurality of hollow deflection tubes, wherein each deflection tube has a first opening at a first end and a second opening at a second end, wherein the first opening of each deflection tube is aligned with the first opening of an adjacent deflection tube such that the first openings are all collinear, and wherein the second openings of the plurality of deflection tubes are staggered with respect to one another;
a plurality of collection tubes corresponding to the plurality of deflection tubes, wherein each collection tube includes an opening positioned to receive a cell passed through and exiting a corresponding deflection tube; and
a current detection circuit coupled to at least one deflection tube.

2. The carrier of claim 1, wherein each deflection tube is electrically insulated.

3. The carrier of claim 1, wherein each collection tube is electrically insulated.

4. The carrier of claim 1, further comprising: a current detection circuit coupled to each deflection tube.

5. The carrier of claim 1, wherein the current detection circuit further comprises: a current-to-voltage converter to detect the presence of a charged drop entering the deflection tube.

6. The carrier of claim 1, wherein the current detection circuit further comprises: an integrator to detect a number of drops per-unit-time entering the deflection tube.

7. The carrier of claim 1, wherein each deflection tube is formed of a metallic material.

8. The carrier of claim 1, wherein each collection tube is formed of a plastic material.

9. The carrier of claim 1, wherein the carrier includes ten or more deflection tubes and ten or more corresponding collection tubes.

10. A system comprising a cell sorter and the carrier of claim 1 wherein the carrier is configured to receive cells from the cell sorter.

11. The cell sorter system of claim 10, further comprising: a computer processor configured to identify when cells passed through a respective deflection tube are not in line with expectations.

12. The cell sorter system of claim 11, further comprising: a motor to move the carrier to a deactivated position.

13. A method for configuring a carrier for receiving cells sorted by a cell sorter system, the method comprising: aligning a plurality of hollow deflection tubes such that a first open end of each deflection tube is positioned collinearly with a first open end of an adjacent deflection tube, and wherein a second open end of each deflection tube is positioned staggered with respect to a second open end of an adjacent deflection tube; positioning a plurality of corresponding collection tubes such that an opening for each collection tube is positioned to receive a cell passed through and exiting a corresponding deflection tube and coupling a current detection circuit to at least one deflection tube.

14. The method of claim 13, wherein each deflection tube is electrically insulated.

15. The method of claim 13, wherein each collection tube is electrically insulated.

16. The method of claim 13, further comprising: coupling a current detection circuit to each deflection tube.

17. The method of claim 13, wherein the current detection circuit further comprises: a current-to-voltage converter to detect the presence of a charged drop entering the deflection tube.

18. The method of claim 13, wherein the current detection circuit further comprises: an integrator to detect a number of drops per-unit-time entering the deflection tube.

19. The method of claim 13, wherein each deflection tube is formed of a metallic material.

20. The method of claim 13, wherein each collection tube is formed of a plastic material.

21. The method of claim 13, wherein the carrier includes ten or more deflection tubes and ten or more corresponding collection tubes.

* * * * *